United States Patent
Benassayag et al.

(10) Patent No.: US 9,498,588 B2
(45) Date of Patent: Nov. 22, 2016

(54) PORTABLE PEN SIZED ELECTRIC HERB VAPORIZER WITH CERAMIC HEATING CHAMBER

(71) Applicant: Atmos Technology, LLC., Davie, FL (US)

(72) Inventors: Charly Benassayag, Miami, FL (US); Yariv Alima, Plantation, FL (US)

(73) Assignee: Atmos Nation, LLC, Davie, FL (US)

( * ) Notice: Subject to any disclaimer, the term of this patent is extended or adjusted under 35 U.S.C. 154(b) by 240 days.

(21) Appl. No.: 13/715,538

(22) Filed: Dec. 14, 2012

(65) Prior Publication Data

US 2013/0152922 A1    Jun. 20, 2013

Related U.S. Application Data

(60) Provisional application No. 61/570,677, filed on Dec. 14, 2011.

(51) Int. Cl.
| | |
|---|---|
| *A61M 15/06* | (2006.01) |
| *A24F 47/00* | (2006.01) |
| *A61M 11/04* | (2006.01) |

(52) U.S. Cl.
CPC ............ *A61M 15/06* (2013.01); *A24F 47/008* (2013.01); *A61M 11/042* (2014.02); *A61M 2205/0211* (2013.01); *A61M 2205/8206* (2013.01)

(58) Field of Classification Search
CPC ............ A61M 15/06; A61M 11/041; A61M 11/042; A61M 11/08; A24F 47/00
USPC ............ 128/200.11–200.14, 202.21, 203.23; 131/194
See application file for complete search history.

(56) References Cited

U.S. PATENT DOCUMENTS

| | | | | |
|---|---|---|---|---|
| 4,771,796 | A * | 9/1988 | Myer ................... | F21L 11/00 131/273 |
| 5,144,962 | A * | 9/1992 | Counts ................. | A24F 47/008 128/200.14 |
| 5,269,327 | A * | 12/1993 | Counts ................. | A24F 47/008 128/200.14 |
| 5,505,214 | A * | 4/1996 | Collins ................. | A24F 47/008 128/202.21 |
| 5,726,421 | A * | 3/1998 | Fleischhauer ......... | A24F 47/008 131/182 |
| 6,532,965 | B1 * | 3/2003 | Abhulimen ........... | A24F 47/004 131/175 |
| 2007/0045288 | A1 * | 3/2007 | Nelson ................. | A61M 11/041 219/533 |
| 2007/0125765 | A1 * | 6/2007 | Nelson ................. | A61M 11/041 219/533 |
| 2007/0267031 | A1 * | 11/2007 | Hon ...................... | A24F 47/008 131/273 |

(Continued)

*Primary Examiner* — Jackie T Ho
*Assistant Examiner* — Joseph D Boecker (57) ABSTRACT

A portable pen sized electric herb vaporizer with ceramic heating chamber is an elongated and cylindrical device used to vaporize the active ingredient of or burn herbs, having a battery, a heating compartment, a chamber connector, and a mouthpiece. Two threaded screw interfaces attach the battery to the heating compartment and the heating compartment to the chamber connector. The mouthpiece holds a ceramic filter and is inserted into the chamber connector. The heating compartment has a ceramic heating chamber within which herbs are placed, and a heating coil connected to the battery within the ceramic heating chamber heats the herbs. The user presses an activator button and inhales through the mouthpiece, drawing heated air over the herbs, through the chamber connector and into the user's lungs. The chamber connector has a disk filter to catch ash and a spring that presses on the herbs for efficient vaporization.

18 Claims, 6 Drawing Sheets

(56) References Cited

U.S. PATENT DOCUMENTS

| | | | | |
|---|---|---|---|---|
| 2008/0257367 A1* | 10/2008 | Paterno | A24F 47/008 | 131/328 |
| 2011/0005535 A1* | 1/2011 | Xiu | A24F 47/008 | 131/273 |
| 2011/0011396 A1* | 1/2011 | Fang | A24F 47/008 | 128/202.21 |
| 2011/0036346 A1* | 2/2011 | Cohen | A61M 15/0065 | 128/200.14 |
| 2011/0226236 A1* | 9/2011 | Buchberger | A61M 11/041 | 128/200.23 |
| 2012/0174914 A1* | 7/2012 | Pirshafiey | A61M 11/041 | 128/200.14 |
| 2012/0255546 A1* | 10/2012 | Goetz | A61M 11/041 | 128/202.21 |
| 2013/0199528 A1* | 8/2013 | Goodman | F22B 1/282 | 128/203.26 |
| 2013/0298905 A1* | 11/2013 | Levin | A24F 47/008 | 128/202.21 |
| 2014/0041655 A1* | 2/2014 | Barron | A61M 11/042 | 128/202.21 |
| 2016/0198771 A1* | 7/2016 | Goggin | A24F 47/008 | 131/329 |

* cited by examiner

PORTABLE PEN SIZED ELECTRIC HERB VAPORIZER WITH CERAMIC HEATING CHAMBER

The current application claims a priority to the U.S. Provisional Patent application Ser. No. 61/570,677 filed on Dec. 14, 2011.

FIELD OF THE INVENTION

The present invention relates generally to consuming herbs. More particularly, the present invention relates to an apparatus for heating herbs in order to extract the active ingredient of plant material by vaporization.

BACKGROUND OF THE INVENTION

In general use, herbs are any plants with leaves, seeds, or flowers used for flavoring, food, medicine, or perfume, or parts of such a plant used in cooking. Herbs have a variety of uses including culinary, medicinal, and in some cases spiritual usage. In medicinal or spiritual use any parts of the plant might be considered to be "herbs", including the leaves, roots, flowers, seeds, bark or berries. Culinary use of the term "herb" typically distinguishes between herbs and spices, with "herbs" referring to fresh or dried leafy green parts of a plant, and spices referring to the other parts of the plant, usually dried.

Plants have the ability to synthesize a wide variety of chemical compounds that are used to perform important biological functions, and to defend against attack from predators such as insects, fungi and herbivorous mammals. Many of these phytochemicals have beneficial effects on long-term or short-term health or mental state when consumed by humans, and many can be effectively used to treat human diseases and other conditions. At least 12,000 such compounds have been isolated so far, which is estimated to be less than 10 percent of the total. Chemical compounds found in plants through mechanisms identical to those already well understood for chemical compounds in conventional drugs, enabling herbal medicines to be as effective as conventional medicines.

Smoking is a practice in which a substance, most commonly tobacco, is burned and the smoke is tasted or inhaled, primarily as a route of administration for recreational drug use, as combustion releases active substances such as nicotine and makes them available for absorption through the lungs. The most common method of smoking today is through cigarettes, which are primarily industrially manufactures but may also be hand-rolled from loose tobacco and rolling paper. Many other smoking implements exist, including cigars, pipes, bidis, hookahs, vaporizers, and bongs. Smoking can be traced back to as early as 5000 BC, and has been recorded in many different cultures around the world. Early smoking evolved in association with religious ceremonies. After the European exploration and conquest of the Americans, the practice of smoking tobacco quickly spread to the rest of the world, eventually introducing a new type of social activity and a form of drug intake which had been previously unknown.

One common alternative to smoking herbs is to use a vaporizer. Vaporization is an alternative to burning that avoids the inhalation of many irritating toxic and carcinogenic by-products. During vaporization, the substance to be vaporized is heated to a temperature below its combustion point but high enough to release the active ingredient. No combustion should occur, so very little ashy smokiness is smelled or tasted. Vapor also ideally contains minimal particulate or tar, and significantly lower concentrations of noxious gases such as carbon monoxide. With little to no smoke produced and cooler temperatures, the irritating and harmful effects of smoking are reduced, as is secondhand smoke.

Many vaporizers on the market are complicated, inconvenient to use, or bulky, making them less than portable, in addition to using methods that provide limited or no filtering of the vapor, require a lighter or butane to use, or require batteries that are only effective for a few uses.

It is therefore an object of the present invention to provide a portable, discreet, pen sized electric herb vaporizer with a ceramic heating chamber and a ceramic filter for improved vaporization and filtration.

DETAIL DESCRIPTIONS OF THE INVENTION

All illustrations of the drawings are for the purpose of describing selected versions of the present invention and are not intended to limit the scope of the present invention.

Figure 1:
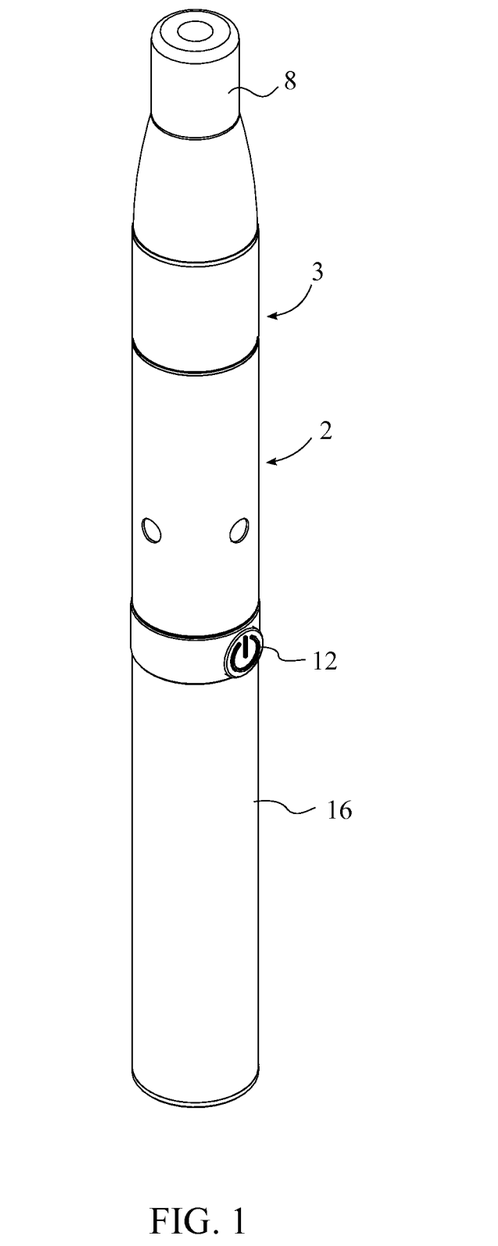
FIG. 1 is a perspective view of the present invention fully assembled.
Figure 2:
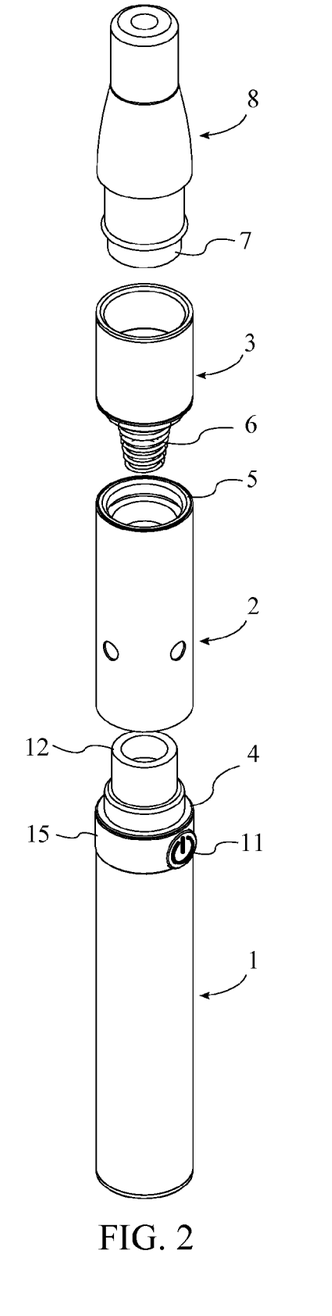
FIG. 2 is an exploded perspective sectional view showing the primary sections of the present invention.

The present invention is a portable pen sized electric herb vaporizer with a ceramic heating chamber 23. The preferred embodiment of the present invention is a device that works in all climates, altitudes, and other circumstances, including, but not limited to, rain, wind, storms or other convenient or inconvenient situations. Referring to FIGS. 1-2, the present invention is generally elongated and cylindrical, similar to the size and shape of a pen and generally comprises a battery 1, a heating compartment 2, a chamber connector 3, a first attachment method 4, a second attachment method 5, a spring 6, a plurality of filters 7, and a mouthpiece 8.

Figure 3:
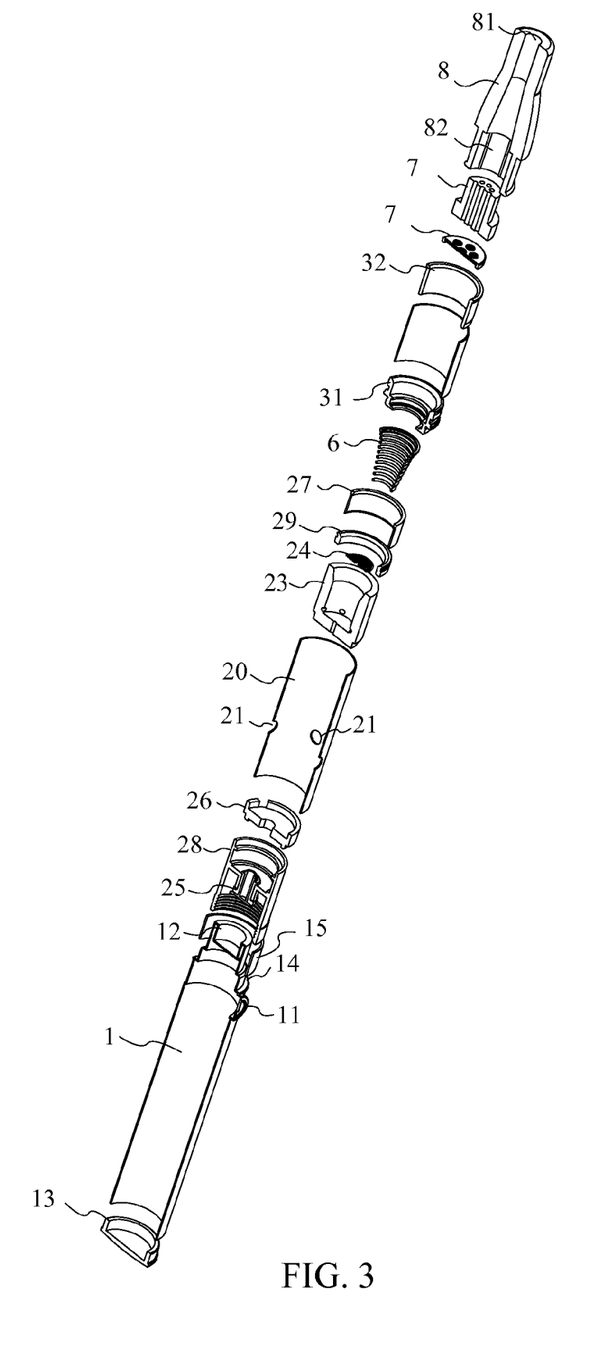
FIG. 3 is an exploded perspective view showing all of the components of the present invention.
Figure 4:
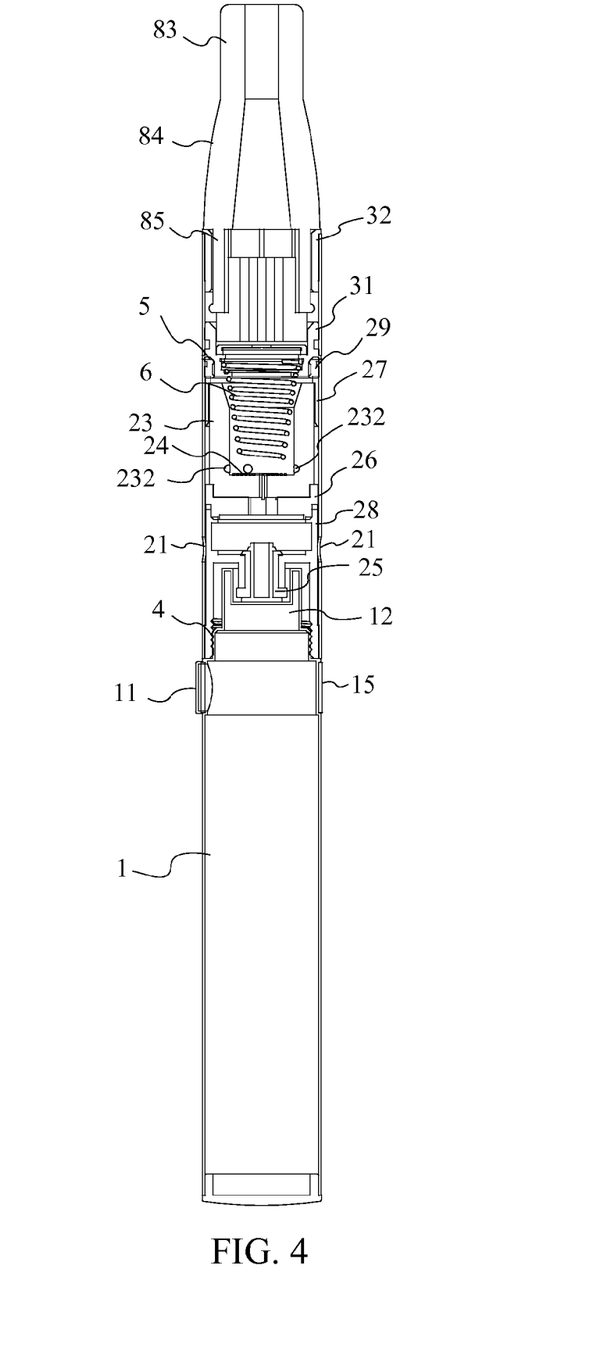
FIG. 4 is a front sectional view of the present invention fully assembled.
Figure 5:
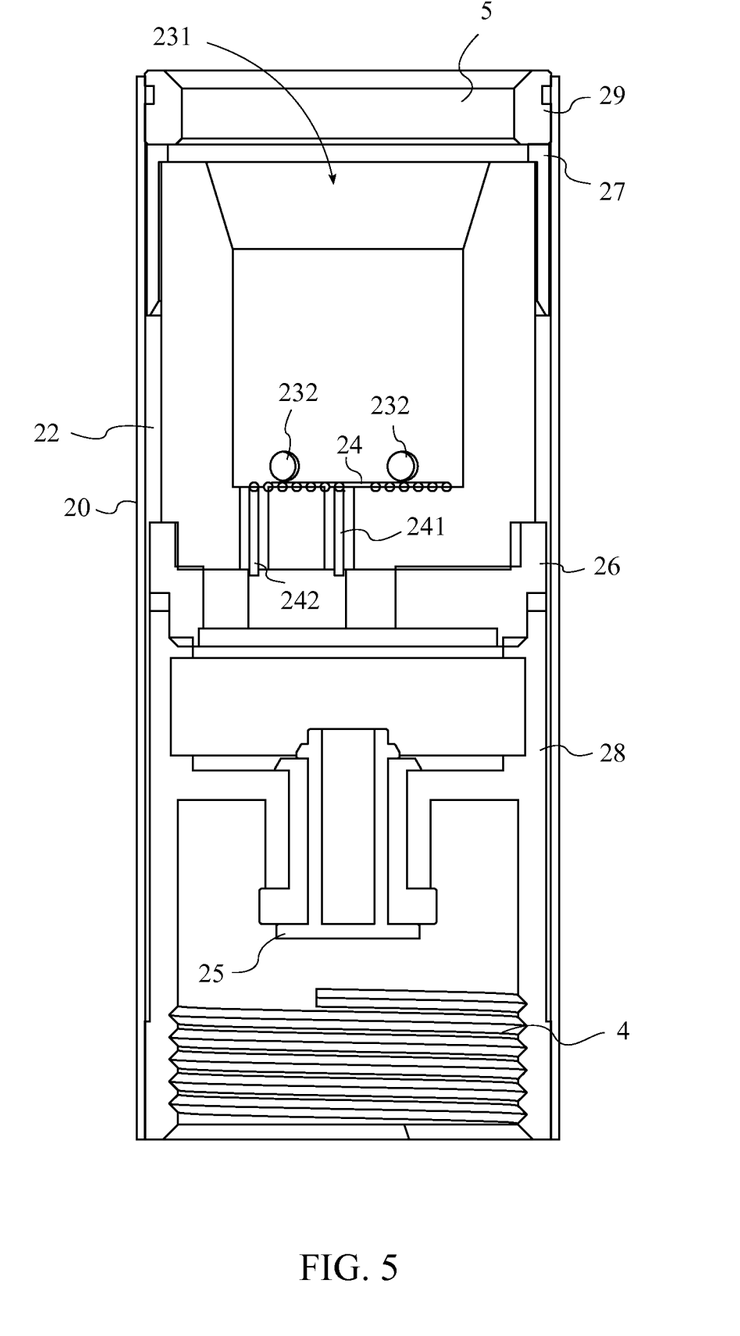
FIG. 5 is a front sectional view of the heating compartment.

Referring to FIGS. 3-5, in the preferred embodiment of the present invention, the heating compartment 2 comprises a cylindrical casing 20, a plurality of air intake holes 21, a radial gap 22, a ceramic heating chamber 23, a heating coil 24, a heater power connection 25, a first spacer 26, a second spacer 27, a first threaded insert 28, and a second threaded insert 29.

Referring to FIG. 2, the battery 1, the heating compartment 2, the chamber connector 3, the spring 6, the plurality of filters 7, and the mouthpiece 8 are positioned concentrically with each other. The battery 1 is positioned adjacent to the heating compartment 2. The chamber connector 3 is positioned adjacent to the heating compartment 2 opposite the battery 1. The mouthpiece 8 is positioned adjacent to the chamber connector 3 opposite the heating compartment 2.

As can be seen in FIGS. 4 and 5, the first attachment method 4 allows the battery 1 to be removably engaged with the heating compartment 2. The second attachment method 5 allows the chamber connector 3 to be removably engaged with the heating compartment 2 opposite the battery 1. The first attachment method 4 and the second attachment method 5 are positioned axially opposite each other along the heating compartment 2. In the preferred embodiment of the present invention, the first attachment method 4 and the second attachment method 5 are each a threaded screw interface. In alternate embodiments of the present invention, the first attachment method 4 and the second attachment method 5 may comprise other means of attaching the heating compartment 2 to the battery 1 and to the chamber connector 3, such as, but not limited to, magnets, snaps, mating parts held in place by friction, twist lock mechanisms or other locking mechanisms.

In the preferred embodiment of the present invention, the battery 1 uses well-known lithium-ion battery technology. In alternate embodiments of the present invention, the battery 1 may use nickel-cadmium battery technology or any other appropriate battery technology. The battery 1 is cylindrical and elongated and comprises an activator button 11, a battery power connection 12, and a button shield ring 15. The button shield ring 15 is preferably made of rubber and is concentrically positioned around the battery 1 and the activator button 11 in order to prevent the activator button 11 from being accidentally pressed while in a user's pocket. In the preferred embodiment of the present invention, at one end of the battery 1 is a translucent cap 13 that shields a light emitting diode that illuminates when the activator button 11 is pressed to indicate when the present invention is in use. The battery power connection 12 is concentrically positioned on the battery 1 opposite the translucent cap 13. The battery power connection 12 is electrically connected to the battery 1. The activator button 11 is exteriorly positioned on the circumference of the battery 1 adjacent to the battery power connection 12. The activator button 11 is electrically connected in between the battery and the battery power connection so that pressing the activator button 11 completes an electrical circuit that allows electrical current to flow from the battery 1 through the battery power connection 12.

In the preferred embodiment of the present invention, the battery power connection 12 is a hollow cylinder concentric with the battery 1 extending from the end of the battery 1 opposite the end with the translucent cap 13. Electrical current is delivered from the battery 1 through the battery power connection 12. The battery power connection 12 comprises a positive battery terminal and a negative battery terminal, which contact with matching terminals on the heater power connection 25 in order to deliver electrical current through the battery power connection 12 to the heating coil 24. In the preferred embodiment of the present invention, the positive battery terminal is the flat concentric surface at the bottom of the battery power connection 12, and the negative battery terminal is on the inner circumference of the battery power connection 12, or at another location separate from the positive battery terminal that contacts with the heater power connection 25 when the battery 1 is engaged with the heating compartment 2. In another embodiment, the positive battery terminal and the negative battery terminal are switched, or another arrangement facilitating an electrical connection between the battery power connection 12 and the heater power connection 25. The battery 1 is removably engaged with the heating compartment 2 by the first attachment method 4. The battery power connection 12 is electrically engaged with the heater power connection 25 when the battery 1 is engaged with the heating compartment 2 by the first attachment method 4. In the preferred embodiment of the present invention, the battery 1 comprises battery threads 14 positioned adjacent to the battery power connection 12 to facilitate the first attachment method 4 between the battery 1 and the heating compartment 2.

Referring to FIGS. 1-5, the heating compartment 2 is cylindrical and is the part of the present invention within which the user places herbs in preparation for heating the herbs and consuming the vapor, smoke or other by-product of heating the herbs. The cylindrical casing 20 is the outer wall of the heating compartment 2, preferably made of brass, that traverses the axial length of the heating compartment 2 and encloses the rest of the components of the heating compartment 2. The cylindrical casing 20 is concentrically positioned between the battery 1 and the chamber connector 3. The plurality of air intake holes 21 is circumferentially positioned around the cylindrical casing 20 and is traversed through the cylindrical casing 20 adjacent to the radial gap 22.

The ceramic heating chamber 23 is generally cylindrical and hollow, comprising an opening 231 at one extremity, resembling a cup shape. The ceramic heating chamber 23 is concentrically positioned within the cylindrical casing 20. The ceramic heating chamber 23 further comprises a plurality of chamber holes 232. The opening 231 and the plurality of chamber holes 232 are positioned opposite each other along the ceramic heating chamber 23. The plurality of chamber holes 232 is circumferentially positioned around the ceramic heating chamber 23 and is traversed through the ceramic heating chamber 23. The plurality of chamber holes 232 is adjacently positioned with the heating coil 24 so that air drawn through the plurality of chamber holes 232 is heated efficiently by the heating coil 24.

Referring to FIG. 5, the radial gap 22 is a cylindrical cavity concentrically positioned between the cylindrical casing 20 and the ceramic heating chamber 23. The outer diameter of the ceramic heating chamber 23 is slightly less than the inner diameter of the cylindrical casing 20, forming the radial gap 22 so that air is allowed to flow from the surrounding environment through the plurality of air intake holes 21, through the radial gap 22 and through the plurality of chamber holes 232 toward the opening 231.

The heating coil 24 is a continuous, elongated, electrically conductive, thin piece of metal that is coiled into a planar spiral shape and is concentrically positioned within the ceramic heating chamber 23 adjacent to the extremity of the ceramic heating chamber 23 opposite the opening 231. The user places herbs within the ceramic heating chamber 23 adjacent to the heating coil 24 through the opening 231. When in use, the heating coil 24 draws electrical current from the battery 1, dissipating power due to the resistivity of the metal and heating the heating coil 24 while the user inhales from the mouthpiece 8, drawing air from the plurality of chamber holes 232 toward the opening 231 and through the mouthpiece 8, causing heated air to pass over the herbs, collecting the desired active ingredient from the herbs. In one embodiment of the present invention, a glass filter is placed adjacent to the heating coil 24 before the herbs are placed into the ceramic heating chamber 24, preventing combustion of the herbs due to direct contact with the heating coil 24 and facilitating efficient vaporization of the active ingredient of the herbs.

The heating coil 24 comprises a positive terminal 241 and a negative terminal 242. The positive terminal 241 and the negative terminal 242 are electrically connected to the heater power connection 25, such that electrical current is allowed to flow from the heater power connection 25 to the heating coil 24 through the positive terminal 241 and the negative terminal 242. The heating coil 24 is electrically connected to the battery power connection 12 through the heater power connection 25 when the heating compartment 2 is engaged with the battery 1 by the first attachment method 4. The positive terminal 241 and the negative terminal 242 may be in any locations that facilitate electrical current being delivered to the heating coil 24 from the battery 1.

The heater power connection 25 is similar to the battery power connection 12. In the preferred embodiment of the present invention, the heater power connection 25 is a cylindrical protrusion with one terminal on the flat extremity of the cylindrical protrusion and the other terminal on the side wall of the cylindrical protrusion, or another location that contacts the battery power connection 12 when the battery 1 is engaged with the heater, or vice versa. The heater power connection 25 is concentrically positioned within the heating compartment 2 adjacent to the ceramic heating chamber 23 opposite the heating coil 24. The heater power connection 25 is electrically connected to the battery power connection 12 when the battery 1 is engaged with the heating compartment 2.

The first spacer 26 is concentrically positioned within the cylindrical casing 20 and is positioned adjacent to the ceramic heating chamber 23 opposite the heating coil 24. The positive terminal 241 and the negative terminal 242 of the heating coil 24 traverse through the ceramic heating chamber 23 and the first spacer 26 in order to facilitate the heating coil 24 being electrically connected to the heater power connection 25. In the preferred embodiment of the present invention, the first spacer 26 is made of silicone rubber.

The first threaded insert 28 is generally cylindrical and concentrically positioned within the cylindrical casing 20, and is preferably made of brass. The first threaded insert 28 is positioned adjacent to the first spacer 26 opposite the ceramic heating chamber 23. The first threaded insert 28 has female threads that interface with the battery threads 14 to facilitate the first attachment method 4 between the battery 1 and the heating compartment 2. The first threaded insert 28 is preferably positioned around the heater power connection 25 and holds the heater power connection 25 in place. In one embodiment of the present invention, the heater power connection 25 is part of the first threaded insert 28.

The second spacer 27 is concentrically positioned within the cylindrical casing 20 between the cylindrical casing 20 and the ceramic heating chamber 23 adjacent to the opening 231, so that the second spacer 27 thermally insulates the cylindrical casing 20 from the ceramic heating chamber 23. In the preferred embodiment of the present invention, the second spacer 27 is made of silicone rubber.

The second threaded insert 29 is concentrically positioned within the cylindrical casing 20 opposite the first threaded insert 28, adjacent to the second spacer 27 opposite the ceramic heating chamber 23. The second threaded insert 29 has screw threads to facilitate the second attachment method 5 between the heating compartment 2 and the chamber connector 3. The second threaded insert 29 is preferably made of brass.

The chamber connector 3 is removably engaged with the heating compartment 2 by the second attachment method 5 opposite the battery 1. The chamber connector 3 comprises a threaded connector insert 31 and a connector sleeve 32. The threaded connector insert 31 and the connector sleeve 32 are positioned concentrically within the chamber connector 3 and opposite each other within the chamber connector 3. The threaded connector insert 31 is generally ring-shaped and has screw threads that facilitate the second attachment method 5 between the heating compartment 2 and the chamber connector 3. The threaded connector insert 31 holds the spring 6 within the chamber connector 3. To engage the chamber connector 3 with the heating compartment 2, the threaded connector insert 31 is engaged with the second threaded insert 29 of the heating compartment 2, completing the second attachment method 5. The connector sleeve 32 is a hollow cylinder and is removably engaged with the filter cavity 82 when the mouthpiece 8 is engaged with the chamber connector 3 by concentrically holding the connector sleeve 32 within the chamber connector 3 by friction.

The spring 6 is concentrically held within the threaded connector insert 31 so that when the chamber connector 3 is engaged with the heating compartment 2 by the second attachment method 5, the spring 6 traverses into the ceramic heating chamber 23, applying force to any herbs placed within the ceramic heating chamber 23 to ensure even heating within the ceramic heating chamber 23. The spring 6 is tapered so that the thinner end of the spring 6 may pass through the threaded connector insert 31 and press against the herbs, while the wider end of the spring 6 has a larger diameter than the inner diameter of the threaded connector insert 31, preventing the spring 6 from entirely passing through the threaded connector insert 31.

Figure 6:
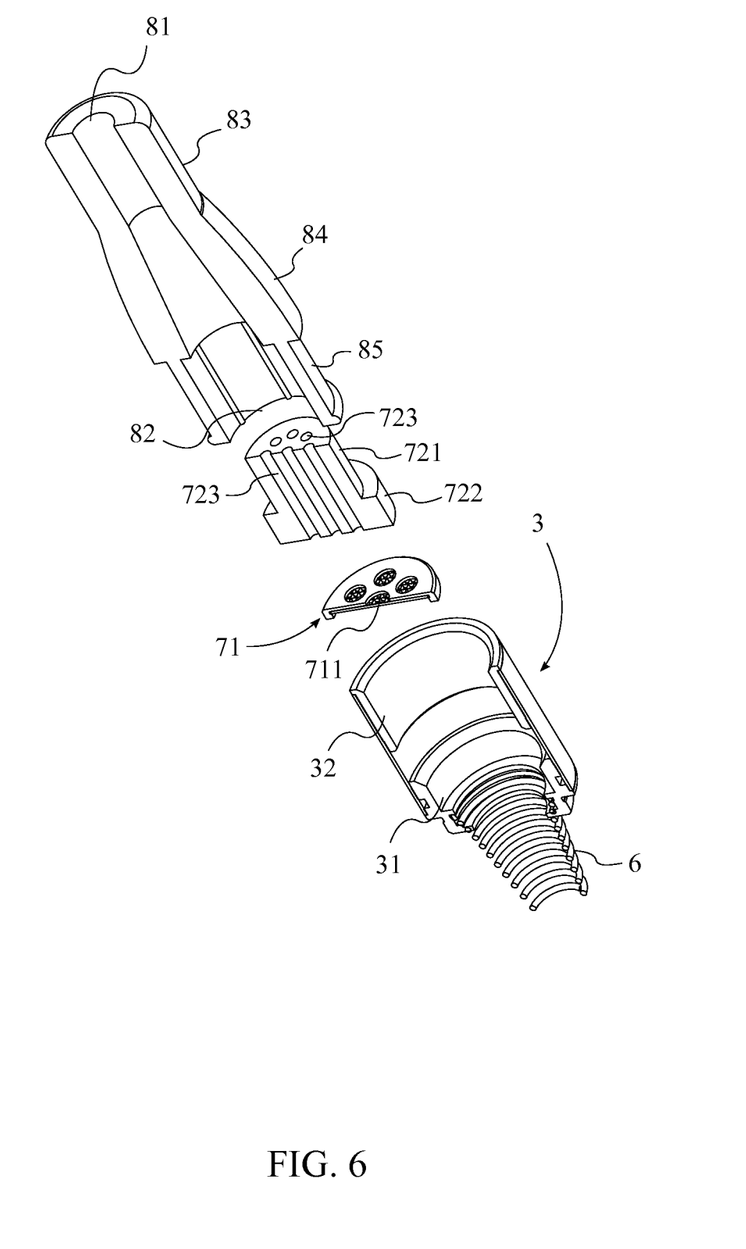
FIG. 6 is an exploded perspective sectional view of the mouthpiece, filters, and chamber connector.

Referring to FIG. 6, the mouthpiece 8 is hollow and has radial symmetry, comprising a mouthpiece section 83, a tapered section 84, and a filter section 85. The filter section 85 has a similar outer diameter to the inner diameter of the connector sleeve 32. The mouthpiece section 83 has a smaller diameter than the filter section 85. The tapered section 84 is positioned between the cylindrical section and the filter section 85, tapering from the diameter of the chamber connector 3 adjacent to the filter section 85 to the diameter of the mouthpiece section 83 adjacent to the mouthpiece section 83. The mouthpiece 8 is removably engaged with the chamber connector 3 opposite the heating compartment 2 by concentrically inserting the filter section 85 into the connector sleeve 32 so that the filter cavity 82 traverses into the chamber connector 3 when the mouthpiece 8 is engaged with the chamber connector 3. The outer diameter of the filter section 85 is similar to the inner diameter of the connector sleeve 32, so that the mouthpiece 8 is held within the chamber connector 3 by friction.

The mouthpiece 8 further comprises a suction hole 81 and a filter cavity 82. The filter cavity 82 is formed by the inner diameter of the filter section 85. The suction hole 81 and the filter cavity 82 are concentrically positioned opposite each other within the mouthpiece 8. The suction hole 81 is formed by the inner diameter of the mouthpiece section 83, and is opposite the filter cavity 82 along the mouthpiece 8, so that air is permitted to flow through the mouthpiece 8 from the filter cavity 82 to the suction hole 81. In the preferred embodiment of the present invention, the mouthpiece 8 is made of silicone rubber.

The plurality of filters 7 is positioned within the chamber connector 3 when the present invention is assembled so that the mouthpiece 8 is engaged with the chamber connector 3. In the preferred embodiment of the present invention, the plurality of filters 7 comprises a disk filter 71 and a ceramic filter 72. The disk filter 71 is a flat disk preferably made of brass, with a plurality of holes cut into the surface of the disk filter 71. The disk filter 71 has a metal mesh weave 711 covering one side of the disk filter 71, so that unwanted particles such as ash, smoke or tar stick to the metal mesh weave 711 as the user inhales the vaporized herb, providing a smoother and healthier inhalation than many pipes and other vaporizers. The disk filter 71 is concentrically positioned between the spring 6 and the ceramic filter 72 within the chamber connector 3 when the mouthpiece 8 is engaged with the chamber connector 3, so that the disk filter 71 rests against the threaded connector insert 31 opposite the spring 6 when the present invention is assembled.

The ceramic filter 72 is radially symmetric, with a first ceramic filter section 721 and a second ceramic filter section 722. The first ceramic filter section 721 is a cylinder with a radius approximately equal to its height. The second ceramic filter section 722 is also a cylinder, concentrically positioned adjacent to the first ceramic filter section 721, with a larger radius than the first ceramic filter section 721 and a smaller height. The ceramic filter 72 comprises a plurality of filter holes 723 that traverse axially through both the first ceramic filter section 721 and the second ceramic filter section 722. The first ceramic filter section 721 is concentrically positioned within the filter cavity 82 of the mouthpiece 8, so that air flow is directed through the plurality of ceramic filter 72 holes when the present invention is in use for further filtering. The inner diameter of the filter cavity 82 is similar to the outer diameter of the first ceramic filter section 721 so that the ceramic filter 72 is concentrically held within the filter cavity 82 by friction and is removable by the user for cleaning or replacement. When the ceramic filter 72 is inserted into the filter cavity 82 and the mouthpiece 8 is inserted into the chamber connector 3, the ceramic filter 72 is positioned adjacent to the disk filter 71 opposite the spring 6 within the chamber connector 3.

To assemble and use the present invention, the spring 6 is placed within the chamber connector 3, the disk filter 71 is placed within the chamber connector 3 adjacent to the threaded connector insert 31 opposite the spring 6, the ceramic filter 72 is inserted into the mouthpiece 8, and the filter section 85 is inserted into the chamber connector 3 through the connector sleeve 32. Herbs are placed within the ceramic heating chamber 23 and the chamber connector 3 is engaged with the heating compartment 2 by the second attachment method 5. The heating compartment 2 is then engaged with the battery 1 and the present invention is ready to use. The user presses the activator button 11, inserts the mouthpiece section 83 into their mouth, and inhales while keeping the activator button 11 pressed.

Although the invention has been explained in relation to its preferred embodiment, it is to be understood that many other possible modifications and variations can be made without departing from the spirit and scope of the invention as hereinafter claimed.

What is claimed is:

1. A portable pen sized electric herb vaporizer comprises,
a battery;
a heating compartment;
a chamber connector;
a spring;
a plurality of filters;
a mouthpiece;
a first attachment method;
a second attachment method;
the battery comprises an activator button and a battery power connection, wherein electrical current is delivered from the battery through the battery power connection;
the heating compartment comprises a cylindrical casing, a plurality of air intake holes, a radial gap, a ceramic heating chamber, a heating coil, and a heater power connection;
the ceramic heating chamber comprises an opening and a plurality of chamber holes;
the battery, the heating compartment, the chamber connector, the spring, the plurality of filters, and the mouthpiece being concentrically positioned with each other;
the battery being positioned adjacent to the heating compartment;
the chamber connector being positioned adjacent to the heating compartment opposite the battery; and
the mouthpiece being positioned adjacent to the chamber connector opposite the heating compartment;
the plurality of filters being positioned within the chamber connector; the plurality of filters comprises a disk filter and a ceramic filter;
the ceramic filter being concentrically held within a filter cavity;
the spring being concentrically held within the chamber connector;
the spring traversing into the ceramic heating chamber; and
the disk filter being positioned between the spring and the ceramic filter within the chamber connector.

2. The portable pen sized electric herb vaporizer as claimed in claim 1 comprises,
the battery power connection being concentrically positioned on the battery;
the battery power connection being electrically connected to the battery;
the activator button being exteriorly positioned on the battery adjacent to the battery power connection; and
the activator button being electronically connected in between the battery and the battery power connection, wherein pressing the activator button completes the electrical circuit that allows electrical current to flow from the battery through the battery power connection.

3. The portable pen sized electric herb vaporizer as claimed in claim 1 comprises;
the cylindrical casing being concentrically positioned between the battery and the chamber connector;
the ceramic heating chamber being concentrically positioned within the cylindrical casing;
the opening and the plurality of chamber holes being positioned opposite of each other along the ceramic heating chamber;
the heating coil being concentrically positioned within the ceramic heating chamber opposite the opening;
the plurality of chamber holes being circumferentially positioned around the ceramic heating chamber;
the plurality of chamber holes being traversed through the ceramic heating chamber and adjacently positioned with the heating coil;
the plurality of air intake holes being circumferentially positioned around the cylindrical casing;
the plurality of air intake holes being traversed through the cylindrical casing;
the radial gap being concentrically positioned between the cylindrical casing and the ceramic heating chamber, wherein air is permitted to flow from the plurality of air intake holes through the radial gap into the plurality of chamber holes; and
the heater power connection being concentrically positioned within the heating compartment adjacent to the ceramic heating chamber opposite the heating coil.

4. The portable pen sized electric herb vaporizer as claimed in claim 3 comprises,
the heating compartment further comprises a first spacer, a second spacer, a first threaded insert, and a second threaded insert;

the first spacer, the second spacer, the first threaded insert, and the second threaded insert being concentrically positioned within the cylindrical casing;

the first spacer being positioned adjacent to the ceramic heating chamber opposite the heating coil;

the first threaded insert being positioned adjacent to the first spacer opposite the ceramic heating chamber around the heater power connection, wherein the first threaded insert facilitates the first attachment method between the battery and the heating compartment;

the second spacer being positioned between the cylindrical casing and the ceramic heating chamber adjacent to the opening, wherein the second spacer thermally insulates the cylindrical casing from the ceramic heating chamber; and the second threaded insert being positioned opposite the first threaded insert within the cylindrical casing adjacent to the second spacer, wherein the second threaded insert facilitates the second attachment method between the heating compartment and the chamber connector.

5. The portable pen sized electric herb vaporizer as claimed in claim 1 comprises, the heating coil comprises a positive terminal and a negative terminal;

the positive terminal and the negative terminal being electrically connected to the heater power connection, wherein electrical current is allowed to flow from the heater power connection to the heating coil through the positive terminal and the negative terminal; and the battery power connection being electrically engaged with the heater power connection, wherein the battery power connection is electrically engaged with the heater power connection when the battery is engaged with the heating compartment.

6. The portable pen sized electric herb vaporizer as claimed in claim 1 comprises, the first attachment method and the second attachment method being positioned axially opposite from each other along the heating compartment;

the battery being removably engaged with the heating compartment by the first attachment method; and the chamber connector being removably engaged with the heating compartment opposite the battery by the second attachment method.

7. The portable pen sized electric herb vaporizer as claimed in claim 1 comprises, the mouthpiece comprises a suction hole and the filter cavity;

the suction hole and the filter cavity being concentrically positioned opposite each other within the mouthpiece, wherein air is permitted to flow through the mouthpiece from the filter cavity to the suction hole;

the mouthpiece being removably engaged within the chamber connector opposite the heating compartment.

8. The portable pen sized electric herb vaporizer as claimed in claim 7 comprises, the chamber connector comprises a threaded connector insert and a connector sleeve;

the threaded connector insert and the connector sleeve being concentrically positioned within the chamber connector;

the threaded connector insert and the connector sleeve being positioned opposite each other within the chamber connector, wherein the threaded connector insert facilitates the second attachment method between the heating compartment and the chamber connector and holds the spring within the chamber connector; and the connector sleeve being positioned around the filter cavity, wherein the filter cavity is concentrically held within the connector sleeve by friction.

9. A portable pen sized electric herb vaporizer comprises, a battery;

a heating compartment;

a chamber connector;

a spring;

a plurality of filters;

a mouthpiece;

a first attachment method;

a second attachment method;

the battery comprises an activator button and a battery power connection, wherein electrical current is delivered from the battery through the battery power connection;

the heating compartment comprises a cylindrical casing, a plurality of air intake holes, a radial gap, a ceramic heating chamber, a heating coil, and a heater power connection;

the ceramic heating chamber comprises an opening and a plurality of chamber holes;

the battery, the heating compartment, the chamber connector, the spring, the plurality of filters, and the mouthpiece being concentrically positioned with each other;

the battery being positioned adjacent to the heating compartment;

the chamber connector being positioned adjacent to the heating compartment opposite the battery; and the mouthpiece being positioned adjacent to the chamber connector opposite the heating compartment;

the cylindrical casing being concentrically positioned between the battery and the chamber connector;

the ceramic heating chamber being concentrically positioned within the cylindrical casing;

the opening and the plurality of chamber holes being positioned opposite of each other along the ceramic heating chamber;

the heating coil being concentrically positioned within the ceramic heating chamber opposite the opening;

the plurality of chamber holes being circumferentially positioned around the ceramic heating chamber;

the plurality of chamber holes being traversed through the ceramic heating chamber and adjacently positioned with the heating coil;

the plurality of air intake holes being circumferentially positioned around the cylindrical casing;

the plurality of air intake holes being traversed through the cylindrical casing;

the radial gap being concentrically positioned between the cylindrical casing and the ceramic heating chamber, wherein air is permitted to flow from the plurality of air intake holes through the radial gap into the plurality of chamber holes;

the heater power connection being concentrically positioned within the heating compartment adjacent to the ceramic heating chamber opposite the heating coil;

the mouthpiece comprises a suction hole and a filter cavity;

the suction hole and the filter cavity being concentrically positioned opposite each other within the mouthpiece, wherein air is permitted to flow through the mouthpiece from the filter cavity to the suction hole;

the mouthpiece being removably engaged within the chamber connect opposite the heating compartment;

the plurality of filters being positioned within the chamber connector; the plurality of filters comprises a disk filter and a ceramic filter;

the ceramic filter being concentrically held within the filter cavity;

the spring being concentrically held within the chamber connector;

the spring traversing into the ceramic heating chamber; and the disk filter being positioned between the spring and the ceramic filter within the chamber connector.

10. The portable pen sized electric herb vaporizer as claimed in claim 9 comprises, the battery power connection being concentrically positioned on the battery;

the battery power connection being electrically connected to the battery;

the activator button being exteriorly positioned on the battery adjacent to the battery power connection; and the activator button being electrically connected in between the battery and the battery power connection, wherein pressing the activator button completes an electrical circuit that allows electrical current to flow from the battery through the battery power connection.

11. The portable pen sized electric herb vaporizer as claimed in claim 9 comprises, the heating compartment further comprises a first spacer, a second spacer, a first threaded insert, and a second threaded insert;

the first spacer, the second spacer, the first threaded insert, and the second threaded insert being concentrically positioned within the cylindrical casing;

the first spacer being positioned adjacent to the ceramic heating chamber opposite the heating coil;

the first threaded insert being positioned adjacent to the first spacer opposite the ceramic heating chamber around the heater power connection, wherein the first threaded insert facilitates the first attachment method between the battery and the heating compartment;

the second spacer being positioned between the cylindrical casing and the ceramic heating chamber adjacent to the opening, wherein the second spacer thermally insulates the cylindrical casing from the ceramic heating chamber; and the second threaded insert being positioned opposite the first threaded insert within the cylindrical casing adjacent to the second spacer, wherein the second threaded insert facilitates the second attachment method between the heating compartment and the chamber connector.

12. The portable pen sized electric herb vaporizer as claimed in claim 9 comprises, the heating coil comprises a positive terminal and a negative terminal;

the positive terminal and the negative terminal being electrically connected to the heater power connection, wherein electrical current is allowed to flow from the heater power connection to the heating coil through the positive terminal and the negative terminal; and the battery power connection being electrically engaged with the heater power connection, wherein the battery power connection is electrically engaged with the heater power connection when the battery is engaged with the heating compartment.

13. The portable pen sized electric herb vaporizer as claimed in claim 9 comprises, the first attachment method and the second attachment method being positioned axially opposite from each other along the heating compartment;

the battery being removably engaged with the heating compartment by the first attachment method; and the chamber connector being removably engaged with the heating compartment opposite the battery by the second attachment method.

14. The portable pen sized electric herb vaporizer as claimed in claim 9 comprises, the chamber connector comprises a threaded connector insert and a connector sleeve;

the threaded connector insert and the connector sleeve being concentrically positioned within the chamber connector;

the threaded connector insert and the connector sleeve being positioned opposite each other within the chamber connector, wherein the threaded connector insert facilitates the second attachment method between the heating compartment and the chamber connector and holds the spring within the chamber connector; and the connector sleeve being positioned around the filter cavity, wherein the filter cavity is concentrically held within the connector sleeve by friction.

15. A portable pen sized electric herb vaporizer comprises, a battery;

a heating compartment;

a chamber connector;

a spring;

a plurality of filters;

a mouthpiece;

a first attachment method;

a second attachment method;

the battery comprises an activator button and a battery power connection, wherein electrical current is delivered from the battery through the battery power connection;

the heating compartment comprises a cylindrical casing, a plurality of air intake holes, a radial gap, a ceramic heating chamber, a heating coil, and a heater power connection;

the ceramic heating chamber comprises an opening and a plurality of chamber holes;

the battery, the heating compartment, the chamber connector, the spring, the plurality of filters, and the mouthpiece being concentrically positioned with each other;

the battery being positioned adjacent to the heating compartment;

the chamber connector being positioned adjacent to the heating compartment opposite the battery; and the mouthpiece being positioned adjacent to the chamber connector opposite the heating compartment;

the battery power connection being concentrically positioned on the battery;

the battery power connection being electrically connected to the battery;

the activator button being exteriorly positioned on the battery adjacent to the battery power connection;

the activator button being electrically connected in between the battery and the battery power connection, wherein pressing the activator button completes an electrical circuit that allows electrical current to flow from the battery through the battery power connection;

the cylindrical casing being concentrically positioned between the battery and the chamber connector;

the ceramic heating chamber being concentrically positioned within the cylindrical casing;

the opening and the plurality of chamber holes being positioned opposite of each other along the ceramic heating chamber;

the heating coil being concentrically positioned within the ceramic heating chamber opposite the opening;

the plurality of chamber holes being circumferentially positioned around the ceramic heating chamber;

the plurality of chamber holes being traversed through the ceramic heating chamber and adjacently positioned with the heating coil;

the plurality of air intake holes being circumferentially positioned around the cylindrical casing;

the plurality of air intake holes being traversed through the cylindrical casing;

the radial gap being concentrically positioned between the cylindrical casing and the ceramic heating chamber, wherein air is permitted to flow from the plurality of air intake holes through the radial gap into the plurality of chamber holes;

the heater power connection being concentrically positioned within the heating compartment adjacent to the ceramic heating chamber opposite the heating coil;

the first attachment method and the second attachment method being positioned axially opposite from each other along the heating compartment;

the battery being removably engaged with the heating compartment by the first attachment method; and the chamber connector being removably engaged with the heating compartment opposite the battery by the second attachment method;

the chamber connector comprises a threaded connector insert and a connector sleeve;

the threaded connector insert and the connector sleeve being concentrically positioned within the chamber connector;

the threaded connector insert and the connector sleeve being positioned opposite each other within the chamber connector, wherein the threaded connector insert facilitates the second attachment method between the heating compartment and the chamber connector and holds the spring within the chamber connector;

the connector sleeve being positioned around a filter cavity wherein the filter is concentrically held within the connector sleeve by friction.

16. The portable pen sized electric herb vaporizer as claimed in claim 15 comprises, the heating compartment further comprises a first spacer, a second spacer, a first threaded insert, and a second threaded insert;

the first spacer, the second spacer, the first threaded insert, and the second threaded insert being concentrically positioned within the cylindrical casing;

the first spacer being positioned adjacent to the ceramic heating chamber opposite the heating coil;

the first threaded insert being positioned adjacent to the first spacer opposite the ceramic heating chamber around the heater power connection, wherein the first threaded insert facilitates the first attachment method between the battery and the heating compartment;

the second spacer being positioned between the cylindrical casing and the ceramic heating chamber adjacent to the opening, wherein the second spacer thermally insulates the cylindrical casing from the ceramic heating chamber; and the second threaded insert being positioned opposite the first threaded insert within the cylindrical casing adjacent to the second spacer, wherein the second threaded insert facilitates the second attachment method between the heating compartment and the chamber connector.

17. The portable pen sized electric herb vaporizer as claimed in claim 15 comprises, the heating coil comprises a positive terminal and a negative terminal; the positive terminal and the negative terminal being electrically connected to the heater power connection, wherein electrical current is allowed to flow from the heater power connection to the heating coil through the positive terminal and the negative terminal; and the battery power connection being electrically engaged with the heater power connection, wherein the battery power connection is electrically engaged with the heater power connection when the battery is engaged with the heating compartment.

18. The portable pen sized electric herb vaporizer as claimed in claim 15 comprises, the mouthpiece comprises a suction hole and the filter cavity;

the suction hole and the filter cavity being concentrically positioned opposite each other within the mouthpiece, wherein air is permitted to flow through the mouthpiece from the filter cavity to the suction hole;

the mouthpiece being removably engaged within the chamber connector opposite the heating compartment;

the plurality of filters being positioned within the chamber connector;

the plurality of filters comprises a disk filter and a ceramic filter;

the ceramic filter being concentrically held within the filter cavity;

the spring being concentrically held within the chamber connector;

the spring traversing into the ceramic heating chamber; and the disk filter being positioned between the spring and the ceramic filter within the chamber connector.

* * * * *